US006927316B1

(12) United States Patent
Faries, Jr. et al.

(10) Patent No.: US 6,927,316 B1
(45) Date of Patent: *Aug. 9, 2005

(54) THERMAL TREATMENT GARMENT AND METHOD OF THERMALLY TREATING BODY PORTIONS

(75) Inventors: Durward I. Faries, Jr., Las Vegas, NV (US); Bruce R. Heymann, Vienna, VA (US); David Hendrix, Ashburn, VA (US)

(73) Assignee: Medical Products, Inc., Chantilly, VA (US)

( * ) Notice: Subject to any disclaimer, the term of this patent is extended or adjusted under 35 U.S.C. 154(b) by 9 days.

This patent is subject to a terminal disclaimer.

(21) Appl. No.: 10/413,565

(22) Filed: Apr. 15, 2003

Related U.S. Application Data (63) Continuation-in-part of application No. 09/635,919, filed on Aug. 10, 2000, now Pat. No. 6,548,728.

(60) Provisional application No. 60/148,271, filed on Aug. 11, 1999.

(51) Int. Cl.[7] .............................................. A61F 13/00
(52) U.S. Cl. .................... 602/43; 602/2; 602/7; 602/14; 602/42; 607/96; 607/108
(58) Field of Search .............................. 602/2, 5, 7, 14, 602/19, 42, 43, 48, 51; 607/96, 114, 108–112; 219/211; 126/204

(56) References Cited

U.S. PATENT DOCUMENTS

| | | | |
|---|---|---|---|
| 1,000,750 A | 8/1911 | Nerli | |
| 2,069,643 A | 2/1937 | Burke | |
| 2,653,601 A | 9/1953 | Morrison | |
| 3,279,465 A | 10/1966 | Chario et al. | |
| 3,343,537 A | 9/1967 | Graham | |
| 3,521,632 A | 7/1970 | Graham | |
| 4,661,099 A | 4/1987 | Von Bittera et al. | |
| 4,671,267 A | 6/1987 | Stout | |
| 4,699,146 A | 10/1987 | Sieverding | |
| 4,909,244 A | 3/1990 | Quarfoot et al. | |
| 4,991,574 A | 2/1991 | Pocknell | |
| 5,005,567 A | 4/1991 | Gilman et al. | |
| 5,038,779 A * | 8/1991 | Barry et al. | 607/108 |
| 5,115,801 A | 5/1992 | Cartmell et al. | |
| 5,156,601 A | 10/1992 | Lorenz et al. | |
| 5,204,110 A | 4/1993 | Cartmell et al. | |
| 5,328,449 A | 7/1994 | Andrews et al. | |

(Continued)

Primary Examiner—Henry Bennett
Assistant Examiner—Amanda Wieker
(74) Attorney, Agent, or Firm—Edell, Shapiro & Finnan, LLC (57) ABSTRACT

A thermal treatment garment of the present invention includes an outer structure layer formed of a pliable material, an interior lining formed of a gel material which directly contacts the wearer skin and a thermal treatment layer to thermally treat and control temperature of the interior lining. The thermal treatment layer heats and/or cools the gel material to a desired temperature and is typically disposed between the structure and gel layers. The thermal treatment layer is controlled by a controller that receives a user-specified or desired temperature. An intervening layer can be disposed between the thermal treatment and structure layers. The intervening layer secures the structure, thermal treatment and/or gel layers to each other and can be an elastomeric material to which the gel and/or thermal treatment layers readily adhere. The garment may be adjustable in size to snugly fit body parts of users in a range of body sizes.

24 Claims, 2 Drawing Sheets

U.S. PATENT DOCUMENTS

| | | |
|---|---|---|
| 5,425,702 A | 6/1995 | Carn et al. |
| 5,527,270 A | 6/1996 | Chase et al. |
| 5,643,189 A | 7/1997 | Masini |
| 5,662,624 A * | 9/1997 | Sundstrom et al. .......... 604/291 |
| 5,682,617 A | 11/1997 | Tumas |
| 5,800,490 A * | 9/1998 | Patz et al. .................. 607/108 |
| 5,935,595 A | 8/1999 | Steen |
| 5,968,003 A | 10/1999 | Sisson |
| 6,071,304 A * | 6/2000 | Augustine et al. ............ 607/96 |
| 6,416,534 B1 * | 7/2002 | Montagnino et al. ....... 607/114 |
| 6,589,270 B2 * | 7/2003 | Augustine .................... 607/96 |
| 2002/0026226 A1 * | 2/2002 | Ein ........................... 607/108 |

* cited by examiner

THERMAL TREATMENT GARMENT AND METHOD OF THERMALLY TREATING BODY PORTIONS

CROSS-REFERENCE TO RELATED APPLICATIONS

This application is a Continuation-in-Part of U.S. patent application Ser. No. 09/635,919, entitled "Wound Dressing Garment" and filed Aug. 10, 2000 now U.S. Pat. No. 6,548,728, which claims priority from U.S. Provisional Patent Application Ser. No. 60/148,271, entitled "Wound Dressing Garment" and filed Aug. 11, 1999. The disclosures of the above-identified patent applications are incorporated herein by reference in their entireties.

BACKGROUND OF THE INVENTION

1. Field of the Invention

The present invention relates to a garment shaped to conform to the contours of and thermally treat body parts and, more particularly, to a garment lined with a thermal element and a self-adhesive sheet-like gel layer forming a garment inner surface to directly contact and thermally treat the skin and/or a wound.

2. Description of the Related Art

Various gel-like materials are known to have properties that promote the healing of wounds such as severe burns. Sheet-like wound dressings having a self-adhesive layer formed of a gel material have been used to treat skin wounds by placing the gel material in direct contact with the wound. These dressings are secured to the wound via adhesion of the gel material to healthy skin surrounding the wound. The gel materials are typically tacky to the touch and readily adhere to the skin, but are easily removed from the skin without significantly pulling the skin or disturbing or clinging to newly formed tissue at the wound site, and leave no perceptible residue. These gel materials tend to manage fluids seeping from the wound in a manner conducive to healing and can be used to deliver additives, such as anti-microbial agents, to the tissue of the wound to prevent infection. In effect, such gel layers operate to seal the wound and function as a synthetic skin.

For example, U.S. Pat. No. 4,661,099 to von Bittera et al., incorporated herein by reference in its entirety, discloses a self-adhesive sheet-like structure having a support layer and an adhesive polyurethane gel layer which adheres to the skin and leaves virtually no residue when removed. The sheet-like structure can be used as a wound dressing in which a gauze bandage is held in place on the wound by the polyurethane gel layer that adheres to the skin surrounding the wound. On dry wounds or wounds having only slight discharge, the polyurethane gel layer can be adapted for use in direct contact with the wound by chemically altering the gel to increase its absorbency.

U.S. Pat. No. 5,115,801 to Cartmell et al., incorporated herein by reference in its entirety, discloses a multi-layer burn dressing having a hydrogel material layer that is placed in direct contact with the burn site on the skin. The hydrogel serves as a bio-compatible, bacterial protective, fluid absorbing, cushioned skin-like medium that facilitates the healing process.

Silicone gel sheets have also been applied directly to damaged skin to treat burns and scars, as disclosed, for example, in U.S. Pat. No. 4,991,574 to Pocknell, incorporated herein by reference in its entirety. In particular, silicone gels have been found to prevent keloid and hypertrophic scaring at wound sites and to reduce the visibility of existing scars. Such silicone gels are manufactured, for example, by Applied Silicon Corporation.

The aforementioned gel dressings are universally produced in flat sheets, with the gel material layer typically being secured to at least a substrate layer providing structural integrity to the dressing. One problem with such dressings is that, while these flat sheets are generally pliable and can be molded to a degree to conform to skin contours, such flat sheets have a limited ability to cover highly contoured skin surfaces of the body (e.g., the face, the scalp, the neck, the shoulders, the hands, the complete torso and/or upper body and arm(s), the complete lower body and/or leg(s), bent elbows and knees, hips, ankles, and feet). Consequently, these sheet-like dressing are generally most suitable for covering only a limited skin area. Further, due to their sheet-like shape, these dressings cannot generally form a secured enclosure to envelop a body part and therefore must rely almost exclusively on the adhesion of the gel material to remain secured to the body.

To cover highly contoured portions of the body, it would be necessary to cut pieces of the sheet dressing to suitable sizes and shapes, and to cover the wound in sections with plural dressing pieces. The set of individual dressing pieces might imperfectly cover the wound, and the cutting and application of customized dressing pieces would be time consuming and would make rapid application of the dressing virtually impossible. Further, this cumbersome operation would have to be performed each time the dressing is changed.

Burn dressings that are shaped to conform to certain portions of the body have long been known in the field. These dressings typically employ conventional wound-contact materials that are absorbent and permeable to fluid and air, such as gauze and fabric. For example, U.S. Pat. No. 3,343,537 to Graham, incorporated herein by reference in its entirety, discloses burn dressings for covering various anatomical parts. The dressings consist of a porous, multi-layer silk lining which comes into contact with the wound, and a multi-layer gauze backing.

U.S. Pat. No. 3,279,465 to Cherio et al., incorporated herein by reference in its entirety, discloses a bandage in the form of a vest having two short sleeves. The bandage consists of a net-like material that holds gauze in place over the wound.

U.S. Pat. No. 5,328,449 to Andrews et al., incorporated herein by reference in its entirety, discloses a wound dressing in the shape of a glove having a porous skin-contacting layer, an absorbent intermediate layer, and an outer layer formed of a water-proof breathable material.

While both gel materials and dressing garments have been used for many years in the treatment of burns and other wounds, to date, no known attempts have been made to develop a dressing garment that employs a skin-contacting gel material. This may be due in part to the fact that sheet-like, gel-based dressings are rather thick, heavy and awkward in comparison to the thin, lightweight, fabric-like materials conventionally used to form dressing garments, and the appearance and gummy, resilient feel of such bulky gel-based dressing sheets do not readily suggest the fashioning of garments from these dressings. The fact that sheet-like, gel-based dressings are conventionally applied via adhesion to a limited skin area, rather than as an enclosure that surrounds or drapes over a body part, further contributes to the perception that sheet-like, gel-based dressings do not lend themselves to use in garments and that these dressings may be ill-suited and impractical for such applications.

Moreover, sheet-like, gel-based dressings are functionally unrelated to conventional burn garments. Sheet-like, gel-based dressings are substantially impermeable to air and moisture, and have limited or no absorbency. The gel material is designed to essentially seal the wound and functions substantially as a synthetic layer of skin over the wound, preventing any external interaction. In contrast, conventional burn garments are formed of permeable, absorbent materials that remove and absorb fluids exuded from the wound. Unlike a synthetic skin, such garments function more as a separate, external covering that rests over the wound and encourages healing of the wound by permitting a controlled flow of air to the wound and a controlled removal of fluid from the wound.

These structural and functional differences between sheet-like, gel-based dressings and conventional burn garments would explain, at least in part, why these wound treatments have existed side-by-side in the field for years without any consideration of possible applications of gel materials in garment-like dressings.

In addition, the healing process and user comfort may be enhanced by warming the gel material (e.g., to temperatures at or near body temperature) and applying the warmed gel material to the skin or wound. However, the above-described related art devices do not provide a manner to thermally treat and control temperature of the gel material, thereby limiting the healing potential of the garments and/or dressings and providing a level of discomfort to the user.

OBJECTS AND SUMMARY OF THE INVENTION

Accordingly, it is an object of the present invention to provide a garment designed to include a thermal element and surround or drape over a highly-contoured body part or a combination of adjacent body parts to thermally treat garment gel material in direct contact with skin located on the body part(s).

It is another object of the present invention to reduce the time required to apply a dressing to a highly contoured portion of the body and to avoid the need to form a customized dressing at the time the dressing is to be applied to the wound.

Yet another object of the present invention is to provide a thermal treatment garment that is adjustable in size to fit a portion of the body for bodies in a range of sizes.

Still another object of the present invention is to rely on the combination of adhesion and conformance to body shape to secure a garment to the skin of a user.

A further object of the present invention is to provide a garment that can be placed on a portion of the body and removed with a minimum of movement of the body and a minimal need to slide the garment over the body.

Yet another object of the present invention is to provide a thermal treatment garment that is easily modifiable to thermally treat only those portions of the body requiring treatment.

The aforesaid objects are achieved individually and/or in combination, and it is not intended that the present invention be construed as requiring two or more of the objects to be combined unless expressly required by the claims attached hereto.

According to the present invention, a garment includes an outer structure layer formed of a pliable material, an interior lining formed of a self-adhesive sheet-like structure made of a gel material which directly contacts the skin or wounds (e.g., burns) on a user and a thermal treatment layer to thermally treat and control temperature of the interior lining. The structure layer provides the overall shape of the garment as well as a framework for supporting the thermal treatment and gel layers. The thermal treatment layer heats and/or cools the gel material to a desired temperature and is typically disposed between the structure and gel layers. The thermal treatment layer is controlled by a controller that receives a user-specified or desired temperature. The structure layer has at least two edge portions that are securable (i.e., either permanently secured or detachably securable) to each other to provide a partial enclosure suitable for enveloping a portion of the body.

The structure layer can include one or more layers of material and can be made of one or more of a variety of materials, such as fabric or elastomeric materials. The structure layer may include plural panels that are permanently secured to each other (e.g., via stitching, fusing or adhesive) along seams. Edges of the structure layer that are detachably securable to each other can be secured using conventional fastening mechanisms, such as hook and loop fasteners.

The self-adhesive, sheet-like gel layer serves as an interior lining of the garment and covers at least a substantial portion thereof, such that the gel layer presents an interior surface for directly contacting the skin of the wearer. The gel layer has a soft, tacky texture and readily adheres to the skin but leaves no perceptible residue on the skin when removed. The gel material does not tend to significantly disturb newly formed tissue at a wound site when removed. Essentially, the gel material functions as a synthetic skin over a wound, allowing the wound to heal with a minimum of interaction with the external environment. By way of example, the gel material can be a silicone gel, a hydrogel or a polyurethane gel.

The gel layer can be coupled to the structure and/or thermal treatment layers by the inherent self-adhesiveness of the gel material, and/or the gel, structure and/or thermal treatment layers can be bonded together by pressure, heat, or a suitable adhesive. An intervening layer can be disposed between the thermal treatment and structure layers. The intervening layer secures the structure, thermal treatment and/or gel layers to each other and can be an elastomeric material to which the gel and/or thermal treatment layers readily adhere. The thermal treatment layer can be attached to the intervening layer by an adhesive or other suitable fastening techniques.

The gel layer is covered with a protective thin, peelable layer, such as a plastic film, to prevent the gel layer from accidentally contacting other surfaces. In operation, the peelable layer is peeled off of the gel layer just before applying the gel layer to the skin of the wearer.

In accordance with one embodiment of the present invention, the garment is made adjustable in size to snugly fit body parts of users in a range of body sizes by allowing the edge portions of the garment to be secured in an overlapped fashion. In particular, the edge portions of the gel and thermal treatment layers are preferably separable from the corresponding edge portions of the structure layer, such that the edge portions of the gel and thermal treatment layers can be overlapped separately from the structure layer. Stated differently, the overlapping edge portions of the gel and thermal treatment layers and the structure layer can be interleaved such that both gel and thermal treatment layer edge portions underlie both structure layer edge portions, with one gel layer edge portion being secured to the other gel layer edge portion (or its coupled thermal treatment layer) and the edge portions of the structure layer being secured to each other via fasteners.

The gel layer can be permanently detached from the garment in the edge region, or the gel layer can be detachable from the garment in the edge region by tugging or peeling the gel layer from the thermal treatment and/or intervening layer. Optionally, the structure layer can be detachable over its entire inner surface from the gel, thermal treatment and/or intervening layers. If a particular wound does not require a gel layer over the entire extent of the garment, this detachability feature allows portions of the gel and thermal treatment layers to be selectively removed to improve the comfort of the garment, while the entire structure layer remains intact to provide complete support for the gel layer and to preserve the ability of the structure layer to secure the garment to the body.

The garment of the present invention can be formed to cover any portion of the body, including any one, combination, or portion of the following body parts: fingers, hands, wrists, elbows, shoulders, arms, the head, the scalp, the face and individual facial features, the neck, the torso, the back, the breasts, the waist, hips, the groin or genitals, legs, knees, ankles, feet, and toes. Thus, the garment of the present invention can be any one, portion or combination of the following: a finger wrap, a glove, a mitt, head or wrist bands, a sleeve, a vest, a jacket or coat, a mask, a skull cap, a neck tube, a girdle, shorts, pants, leggings, a leg wrap, a sock, a toe wrap, scarf, undergarment, blanket (e.g., baby, quilt, etc.), bed sheet, etc.

The above and still further objects, features and advantages of the present invention will become apparent upon consideration of the following detailed description of specific embodiments thereof, particularly when taken in conjunction with the accompanying drawings wherein like reference numerals in the various figures are utilized to designate like components.

DETAILED DESCRIPTION OF THE PREFERRED EMBODIMENTS

Figure 1:
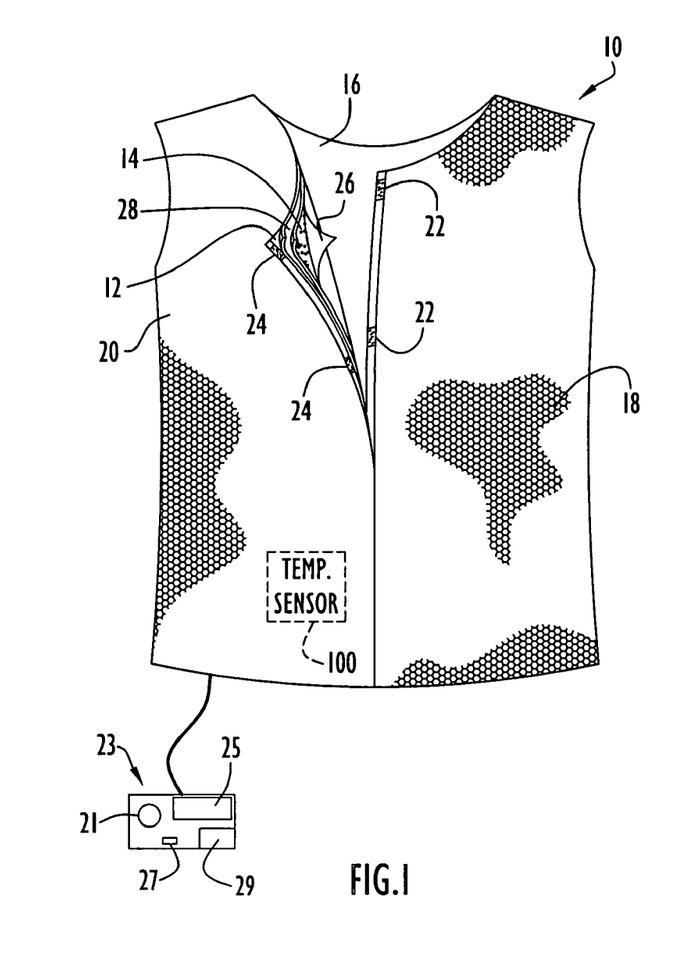
FIG. 1 is front view in elevation of a thermal treatment garment for a human torso in accordance with an exemplary embodiment of the present invention.

A thermal treatment garment in accordance with an exemplary embodiment of the present invention for thermally treating skin or wounds (e.g., burns, scars, etc.) is illustrated in FIG. 1. The garment includes a thermal element to heat or cool the garment to a desired temperature as described below. The garment may be utilized for treatment of wounds, such as burns or scars, or may be employed to heat or cool user body portions (e.g., warm users in cold weather or environments and/or during skiing or other cold weather activities, cool users in hot weather or environments or during activities leading to perspiration, etc.). Specifically, the exemplary garment takes the form of a sleeveless vest 10 that is shaped and sized to envelop the torso of the human body. As used herein, the term "envelop" means to substantially cover by enclosing, encasing, surrounding or fitting over a portion of the body, such that the correspondence between the shape of the garment and the covered portion of the body generally contributes to keeping the garment secured on the portion of the body. It will be understood that the term "envelop" does not require that an entire body part be covered; thus, for example, a portion of an arm can be enveloped while another portion of the arm or the hand can remain uncovered. It will be further understood that, while the garment of the present invention is configured to envelop a portion or all of a body part or plural body parts, the garment may include one or more openings for adjacent body parts (e.g., a torso garment may include openings for the waist, neck and arms, and a glove-like garment may include an opening for the arm). Thus, as used herein, the term "partial enclosure" refers to an enclosure that has at least one opening through which a body part adjacent a site can extend.

Exemplary garment 10 includes an outer structure layer 12 formed of a pliable material, an inner lining gel layer 14 formed of a self-adhesive, sheet-like gel material suitable for contacting skin or treating wounds (e.g., severe burns or scars) and a thermal treatment layer 28 typically disposed between the structure and gel layers. In the embodiment shown in FIG. 1, structure layer 12 is formed of a mesh fabric made of nylon or the like. Structure layer 12 provides the overall shape of the garment and provides a framework for supporting gel layer 14. Structure layer 12 of sleeveless vest garment 10 includes three mesh fabric panels sewn together at their edges. Specifically, garment 10 includes a back panel 16 sewn along part of one side edge and part of the top edge to a front left panel 18 (e.g., the left panel with respect to a wearer as viewed in FIG. 1), and along part of another side edge and part of the top edge to a front right panel 20 (e.g., the right panel with respect to a wearer as viewed in FIG. 1), leaving arm and neck openings between the panels. The edges of the panels that are sewn together have complementary shapes forming seams that correspond to contours of the portion of the body over which the seams of the garment fit (in this case, the shoulders and the sides of the torso).

In addition to providing the shape and framework of the garment, structure layer 12 supplements gel layer 14 in securing the garment to the portion of the body (in this example, the torso). Specifically, front left and right panels 18 and 20 meet, but are not permanently attached, along a vertical (as worn on the body) centerline extending from the front center of the neck opening to the bottom of the garment at the front center of the waistline. Front left and right panels 18 and 20 are detachably securable to each other along the front vertical centerline with a fastener. The fastener can be any one or a combination of conventional fastening mechanisms, including, but not limited to: hook and loop fasteners, buckles, buttons, clasp or clipping mechanisms, snaps, straps with locking rings, zippers, string or fabric ties, straps or frictional force.

By way of example, exemplary garment 10 shown in FIG. 1 includes complementary hook and loop fasteners 22 and 24 respectively attached to the corresponding edges of the left and right front panels of structure layer 12. Fasteners 22 and 24 engage each other to secure together the left and right front panels 18 and 20 along the front vertical center-line of garment 10. By securing the open edges of structure layer 12 with fasteners, structure layer 12 forms a partial enclosure that augments the gel layer in keeping the garment securely attached to the body. Further, the detachability of the left and right front panels 18 and 20 allows sleeveless vest garment 10 to be placed over and secured to the torso with a minimum of movement of the torso and garment 10 and with a minimum of contact between the torso and gel layer 14 of garment 10 prior to correctly positioning garment 10 on the torso.

As used herein and in the claims, the term "securable" is used broadly to describe both edge portions that are permanently secured to each other and edge portions that are detachably securable (e.g., with fasteners). As will be understood from the foregoing description, structure layer 12 of garment 10 includes edges that are permanently secured to each other along seams as well as edges that are detachably securable to each other with fasteners. However, as will be evident from other embodiments described and shown herein, the present invention is not limited to embodiments of garments having both permanently secured edges and detachably securable edges.

While shown in FIG. 1 as a nylon mesh fabric, the structure layer of the present invention is not limited to any particular material or combination of materials. The structure layer can comprise one or more layers formed of one or more materials, including, but not limited to: woven fabrics and textiles formed of natural and/or synthetic materials, non-woven fabrics and textiles formed of natural and/or synthetic materials, and elastomeric materials.

Self-adhesive, sheet-like gel layer 14 serves as an interior lining of garment 10 and is coupled to an inner surface of the garment to cover at least a substantial portion thereof, such that gel layer 14 presents an interior surface for directly contacting the skin of the wearer. Gel layer 14 can be described as a soft, tacky, non-friable gel sheet that readily adheres to skin and that leaves no perceptible residue (e.g., no sticky or gummy residue) on the skin when removed. While described as sheet-like, it will be understood that the gel layer need not be planar, and may be curved or arcuate in one or more dimensions as required to conform to the shape of the garment. The gel material is slightly adhesive to skin, but does not tend to significantly disturb newly formed tissue at a wound site when removed. The gel material essentially functions as a synthetic skin over a wound, allowing the wound to heal with a minimum of interaction with the external environment.

The gel material of gel layer 14 can be, for example a semi-occlusive silicone gel, such as a silicone gel manufactured, for example, by Applied Silicon Corporation. Such silicone gels have been used in the treatment of burns and scars. Specifically, silicone gel sheeting has been found to improve wound healing, reduce pain, and produce a better cosmetic resulting by flattening and softening hypertrophic and keloid scar tissue and returning the skin to its natural color. However, any other suitable gel materials may be utilized (e.g., hydrogels, polyurethane gels, etc.). Further, the gel material is beneficial to skin to assist with dry skin or cracking, corns, bunions, scarring and other skin disorders. Optionally, additives (e.g., anti-microbial agents, Aloe, Vitamin E or other vitamins, medicaments, lotions, ointments, etc.) can be incorporated or infused in the gel material to enhance the skin and/or prevent infection of a wound. In this case, the gel material further serves as an osmotic absorption or semi-permeable membrane to enable the additives to directly enter the skin or wound.

By way of non-limiting example, gel layer 14 can be approximately one-eighth to one-sixteenth of an inch in thickness or approximately one to five millimeters in thickness. It is to be understood that these dimensions are provided by way of example only and are not in any way limiting on the scope of the invention. Gel layer 14 can be secured to the interior surface of the garment in a variety of ways. In the exemplary embodiment shown in FIG. 1, gel layer 14 directly contacts and is secured to thermal treatment layer 28, at least in part, by the inherent self-adhesiveness of the gel material. The bond between structure layer 12, gel layer 14 and thermal treatment layer 28 can be formed by any one or a combination of: pressure (e.g., pressing the layers together), heat, and a suitable adhesive. The gel layer sheeting and thermal treatment layer can be bonded to the panels of the structure layer prior to securing the panels together, or the panels of structure layer 12 can be secured together prior to lining the garment with gel layer 14 and thermal treatment layer 28. In either case, gel layer 14 can comprise a plurality of sheets shaped and sized to line the desired portion of the garment. As explained in greater detail below, to provide maximum utility, the sheet or sheets of gel layer 14 preferably cover substantially all of the interior of the garment, with gel layer 14 being separable or peelable from the garment so that selected portions of gel layer 14 can be removed when not required to cover a particular body portion or wound.

Prior to application to the skin, gel layer 14 is covered with a protective thin, peelable layer 26, such as a plastic film, to prevent gel layer 14 from accidentally contacting other surfaces. In operation, peelable layer 26 is peeled off of gel layer 14 just before applying the gel layer to the skin of the wearer.

Thermal treatment layer 28 is disposed between structure layer 12 and gel layer 14 as described above. The thermal treatment layer may be of any shape or size and is typically dimensioned to substantially cover gel layer 14. The thermal treatment layer may be secured or fastened to the structure and/or gel layers via any conventional or other techniques (e.g., sewing, adhesives, the gel layer adhesiveness, etc.). Alternatively, the thermal treatment layer may be placed in or on the garment or garment layers at any suitable locations (e.g., on the garment exterior, between the structure and gel layers, between plural gel layers, in direct contact with the skin, etc.). Thermal treatment layer 28 thermally treats and controls the temperature of gel layer 14. The gel layer basically serves as a thermal conductor to distribute thermal energy from the thermal treatment layer to a wearer in a substantially uniform manner.

The thermal treatment layer generally heats the garment and may be implemented by a conventional etched foil silicon rubber heating pad. Alternatively, heating wires or coils may be secured to or disposed within a suitable housing or structure (e.g., plastic layer, pad or platform mounting the coils or wires, etc.) to form thermal treatment layer 28. The garment may be utilized to warm wearers in cold environments or to assist healing by heating the gel material covering a wound as described above. Further, the garment heating may assist with circulatory problems and/or dissolving blood clots in any body portions or extremities. A controller 23 is coupled to and controls thermal treatment layer 28 to heat the garment to a desired temperature.

A temperature sensor (not shown) is disposed within the garment to provide a temperature indication to controller 23. The temperature sensor may be disposed proximate the wearer or the thermal treatment, structure or gel layers and may be implemented by any conventional or other temperature sensor (e.g., RTD, infrared, etc.) to provide a temperature indication (e.g., of the structure, gel or thermal treatment layers, wearer, etc.). The controller utilizes the temperature indication to control the thermal treatment layer accordingly to heat the garment to a desired temperature. In particular, the controller controls power to the thermal treatment layer. If the temperature indication from the temperature sensor is equal to or exceeds a desired or user-specified temperature, controller 23 disables power to thermal treatment layer 28. When the temperature indication from the temperature sensor is less than the desired temperature, the controller enables power to the thermal treatment layer.

Controller 23 may be implemented by any conventional or other microprocessor, controller and/or circuitry. The controller includes a power switch 21, display 25, controls or input devices 27 and a power source 29. Power switch 21 is a conventional switch to control power to the controller, while power source 29 is typically implemented by batteries in order to enable the controller to be transportable with garment 10. Display 25 may be implemented by any conventional or other display (e.g., LCD, LED, etc.) and displays the measured and/or desired temperatures and other information (e.g., time, date, etc.). Input devices 27 (e.g., buttons, keys, etc.) enable entry of a desired temperature and other information by a user and facilitate control of display 25 to display the actual and/or set point temperatures and other information.

The thermal treatment layer may alternatively be implemented by a thermoelectric device, such as a Peltier chip, to heat and cool the garment to a desired or user-specified temperature. The thermal treatment layer may include a housing or structure (e.g., pad or platform, etc.) with heat sinks coupled to the thermoelectric device to provide heating and cooling. The thermoelectric device basically enables one or more heat sinks to absorb thermal energy (e.g., thereby cooling the surrounding environment), while enabling one or more other heat sinks to expel thermal energy (e.g., thereby heating the surrounding environment) based on the direction of current or voltage polarity applied to the device. The heat sinks are basically dispersed throughout the thermal treatment layer and disposed proximate the wearer, or the structure or gel layers as described above. Controller 23 controls the polarity and/or distribution of power to the thermoelectric device to control heating and cooling of the garment by the heat sinks to the desired temperature. In particular, the temperature sensor provides a temperature indication to controller 23 as described above. If the temperature indication from the temperature sensor is equal to or exceeds a desired or user-specified temperature, controller 23 provides a particular polarity to the thermoelectric device to enable the heat sinks to cool the garment. When the temperature indication from the temperature sensor is less than the desired temperature, the controller provides an opposing polarity to the thermoelectric device to enable the heat sinks to heat the garment. The thermoelectric device may be configured to only heat or cool the garment, where the controller may control (e.g., enable or disable) power to the device accordingly to attain a desired garment temperature. The garment heating and cooling may be utilized to assist healing or warm or cool wearers in various environments or during activities (e.g., workouts, at the beach, etc.). Further, the garment may serve as a hot or cold compress to treat various wounds, bruises and muscle injuries (e.g., pulls, strains, sprains, swelling or inflammation, etc).

The thermal treatment layer may further be embedded within the garment structure and/or gel layers. For example, the heating pad or wires may be disposed within the structure and/or gel layers to heat the garment. Similarly, the heat sinks may be disposed within the structure and/or gel layers to heat and cool the garment.

In operation, vest 10 is placed on a wearer with gel layer 14 in contact with the skin or wound. The wearer enables power to controller 23 via power switch 21 and enters a desired temperature into the controller through input devices 27. The controller controls the polarity and/or distribution of power to the thermal treatment layer in response to a temperature indication from the temperature sensor to attain a desired garment temperature as described above. The gel material may include or be infused with various types of medicaments to assist with wounds or skin conditions as described above. When the session is completed, the wearer disables power to the controller via power switch 21 and removes vest 10.

Figure 2:
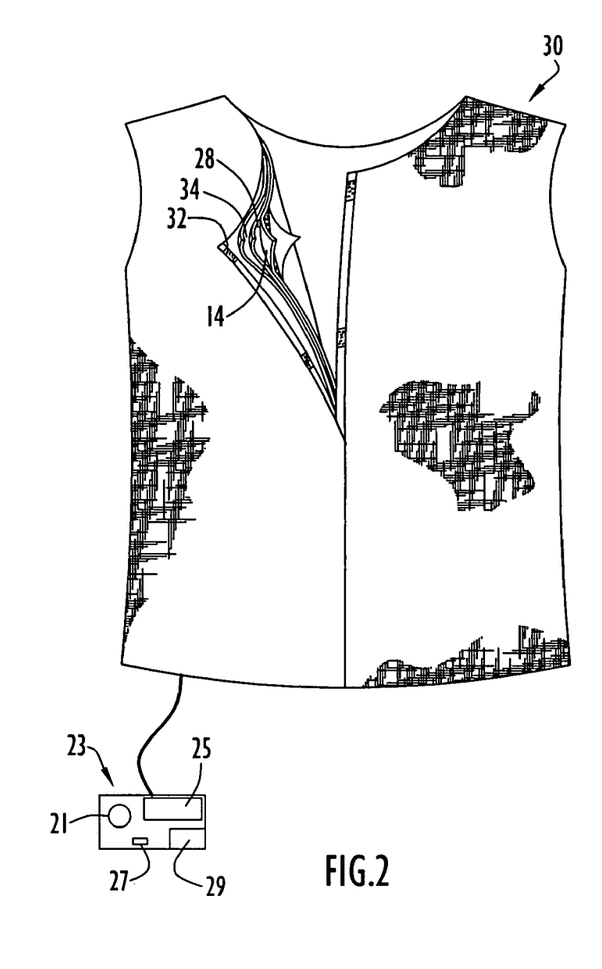
FIG. 2 is a front view in elevation of a thermal treatment garment for a human torso in accordance with another embodiment of the present invention.

Referring to FIG. 2, a thermal treatment garment 30 in accordance with another embodiment of the present invention includes a structure layer 32, gel layer 14 and thermal treatment layer 28. The structure, gel and thermal treatment layers are substantially similar to the layers described above. Structure layer 32 is formed of a fabric material and is coupled to thermal treatment layer 28 via an intervening layer 34. Intervening layer 34 can be, for example, a galvanized or ungalvanized elastomeric material to which the thermal treatment and/or gel layers readily adhere. The gel and thermal treatment layers reside on one side of intervening layer 34, while structure layer 32 is disposed on the other side of intervening layer 34. The thermal treatment and structure layers may be permanently or removably attached to the intervening layer via any conventional or other techniques (e.g., sewing, adhesives, the gel material adhesiveness, etc.). In addition to serving as a base layer to which structure layer 32, thermal treatment layer 28 and/or gel layer 14 can be readily attached, intervening layer 34 also provides additional overall strength to the gel sheeting without significantly reducing the flexibility of the gel sheeting. The thermal treatment layer is coupled to and controlled by controller 23 to thermally treat garment 30 to a desired temperature in accordance with a temperature sensor measurement in substantially the same manner described above. The temperature sensor may be disposed within the garment at any location (e.g., proximate the wearer or the gel, structure, intervening or thermal treatment layers, etc.).

It will be readily understood that other structure layer configurations fall within the scope of the invention. For example, the structure layer can comprise any number of layers, or the structure layer can be formed of a single elastomeric layer without any fabric layers. In accordance with another embodiment, the structure layer is formed using a molding technique wherein the structure layer comprises a material shaped by setting in a mold.

Where the structure layer includes a plurality of panels permanently secured to each other along seams (see FIGS. 1–3 and 5), the panels of the structure layer can be secured along the seams by sewing, stitching, staples or any other suitable mechanism. For example, where the panels of the structure layer comprise an elastomeric or thermoplastic material, the panels can be secured at their edges by heat fusing.

Figures 3, 4:
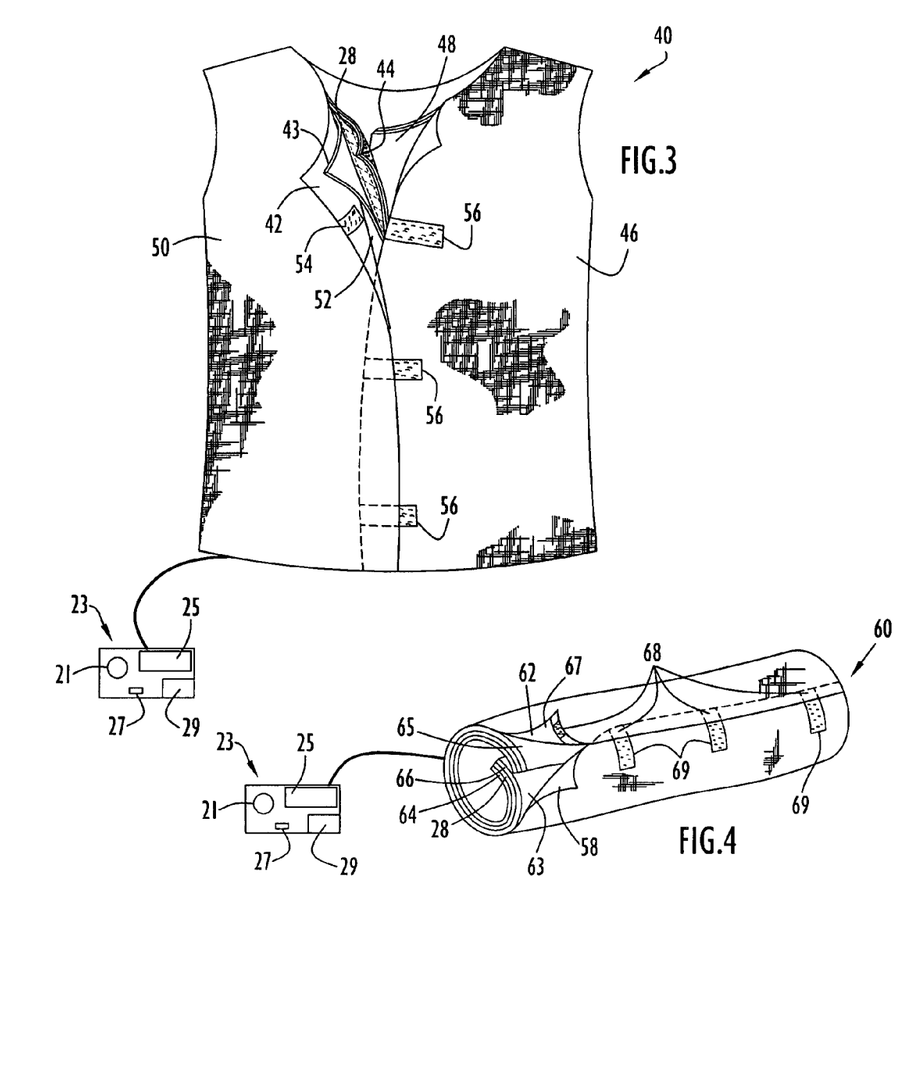
FIG. 3 is front view in elevation of an adjustable thermal treatment garment for a human torso in accordance with another embodiment of the present invention.
FIG. 4 is a perspective view of an adjustable thermal treatment garment for a human arm in accordance with another embodiment of the present invention.

In accordance with another embodiment of the present invention, a thermal treatment garment is adjustable in size to snugly fit body parts in a range of sizes. Referring to FIG.

3, an adjustable thermal treatment garment 40 for the torso includes a structure layer 42, an intervening elastomeric layer 43, an inner gel layer 44 and a thermal treatment layer 28. The layers and arrangement are similar to those shown in FIG. 2, except that thermal treatment layer 28, intervening elastomeric layer 43 and gel layer 44 are detached or detachable from structure layer 42 at least in the vicinity of the edges of the structure layer that are securable with fasteners. Specifically, a front left panel 46 (e.g., the left panel with respect to a wearer as viewed in FIG. 3) of structure layer 42 is detached from edge portion 48 of underlying thermal treatment, intervening and gel layers 28, 43 and 44 along the entire vertical edge of the front left panel over a distance of at least an inch, and preferably at least two inches, in the horizontal direction. Similarly, a front right panel 50 (e.g., the right panel with respect to a wearer as viewed in FIG. 3) of structure layer 42 is detached from edge portion 52 of underlying thermal treatment, intervening and gel layers 28, 43 and 44 along the entire vertical edge of the front right panel over a distance of at least an inch, and preferably at least two inches, in the horizontal direction. As seen in FIG. 3, edge portions 48 and 52 are essentially flaps in the shape of vertical strips extending along the front vertical centerline of garment 40 in parallel with edges of structure layer 42. The overall size of the garment is selected to be at least as large as necessary to cover the torso of a wearer, such that, when gel layer 44 is smoothly attached to the skin of the torso, left and right edge portions 48 and 52 overlap along the front vertical centerline of the garment. For example, right edge portion 52 of the thermal treatment, intervening and gel layers overlaps and extends over left edge portion 48, but extends underneath left front panel 46 of structure layer 42. Gel layer 44 of the overlying right edge portion readily adheres to left edge portion 48 of underlying intervening layer 43, thereby snugly sealing gel layer 44 to the torso (alternatively, the overlapping portion of the edge portion can be trimmed off).

The detached portions of left and right front panels 46 and 50 of structure layer 42 also form overlapping flaps. In the foregoing example, the edge portion (flap) of right front panel 50 overlaps and extends over the edge portion of left front panel 46. A set of adjustable fasteners 54 and 56 respectively attached to left and right front panels 46 and 50 are used to secure the edge portions of the front panels to each other in the overlapped position. By way of non-limiting example, fasteners 54 and 56 can be complementary hook and loop fasteners. To account for variation in the degree of overlap, the fasteners of at least one of the sets of fasteners 54 and 56 extend longitudinally in the horizontal direction (i.e., transversely of the garment body) to permit engagement of the fasteners over a range of overlap positions. In the preferred embodiment, the fasteners are rectangular. Adjustable length straps or any other type of adjustable position fasteners can be used with adjustable garment 40.

The adjustability of the garment permits a wide range of body sizes to be fit with a limited number of different-sized garments (e.g., small, medium, large, extra large). The thermal treatment layer is coupled to and controlled by controller 23 to thermally treat garment 40 to a desired temperature in accordance with temperature sensor measurements in substantially the same manner described above.

As will be understood from the foregoing, an important aspect of the adjustable garment of this embodiment of the present invention is the region of detachment between the outer structure layer and the inner gel layer in the vicinity of the edges of the structure layer that are secured via fasteners. This detachment region permits the gel layer and the structure layer to be independently overlapped and independently secured to provide a superior fit. Specifically, the overlapping portion of the gel layer can slide underneath the opposing edge of the structure layer and adhere directly to the opposing (overlapped) gel layer (or the elastomeric backing of the gel layer), thermal treatment layer or intervening layer. That is, a first gel layer edge portion can be interleaved between a second, opposing gel layer edge portion and a second, opposing structure layer, with a second structure layer edge portion being interleaved between a first intervening layer edge portion and its corresponding first structure layer. Further, the two edges of the structure layer can be overlapped and fastened to each other without interference from the other garment layers (e.g., gel, thermal treatment and/or intervening layers), thereby permitting a simple fastener design.

While described as having both left and right detached layer flaps, it will be understood that a similar result can be obtained by forming a detached layer flap along only one of the left and right edges of the front panels. In this case, independent overlapping is achieved by extending a first structure layer edge portion and its attached first layer edge portion between a second intervening layer edge portion and a second structure layer edge portion that has been separated from the second intervening layer edge portion.

The gel layer can be permanently detached (i.e., separated) from the structure, intervening and/or thermal treatment layers in the edge region, or the gel layer can be detachable from the structure, intervening and/or thermal treatment layers in the edge region (as used herein and in the claims, the term "separable" is used broadly to describe both permanently detached edge portions and detachable edge portions or layers). Specifically, outer structure layer 42 can be peelable from intervening layer 43 at least in the vicinity of the front vertical centerline edges of garment 40. Preferably, a significant degree of tugging force is required to tug or peel apart structure layer 42 and intervening layer 43 so that these layers are not readily susceptible to being unintentionally detached.

Optionally, the structure layer can be detachable over its entire inner surface from the thermal treatment and gel layers (or an intervening layer). If a particular wound does not require a gel layer over the entire extent of the garment, this detachability feature allows portions of the thermal treatment and gel layers to be selectively removed to improve the comfort of the garment, while the entire structure layer remains intact to provide complete support for the gel and thermal treatment layers and to preserve the ability of the structure layer to secure the garment to the body. In this case, the thermal treatment layer may be formed of a plurality of thermal units that are controlled by the controller in the manner described above to thermally treat the garment. The thermal units may be detached from the vest and controller. Alternatively, the thermal treatment layer may remain intact to thermally treat a wearer after detachment of gel layer portions.

According to another embodiment of the adjustable garment, the structure and gel layers are not detached, and one edge of the garment overlaps and extends over the other edge of the garment, and adjustable fasteners, such as straps, secure the exterior of the garment. While this embodiment may be simpler in some respects, the overlapping portion of the gel layer may have only limited adhesion to the underlying structure layer, and the design of the adjustable fasteners may be limited by absence of a structure layer flap detached from the gel layer.

While the garment of the present invention has been shown in FIGS. 1–3 as a sleeveless vest for covering the torso, it will be understood that the present invention includes garments or other articles that cover any portion of the body, including, but not limited to, any one, combination, or portion of the following body parts: fingers, hands, wrists, elbows, shoulders, arms, the head, the scalp, the face and individual facial features, the neck, the breasts, the torso, the back, the waist, hips, the groin or genitals, legs, knees, ankles, feet, and toes. Thus, the garment of the present invention may take a number of different forms, including, but not limited to: a finger wrap, a glove, a mitt, head or wrist bands, a sleeve, a vest, a jacket or coat, a mask, a skull cap, a neck tube, a girdle, shorts, pants, leggings, a leg wrap, a sock, a toe wrap, a scarf, an undergarment, blanket (e.g., for babies, a quilt, etc.), bed sheet, etc.

Referring to FIG. 4, an adjustable thermal treatment garment in the form of a sleeve 60 for on an arm is shown. Sleeve 60 includes an outer structure layer 62, an intervening elastomeric layer 63, an inner gel layer 64 and thermal treatment layer 28. The structure, gel, intervening and thermal treatment layers and arrangement are similar to those described above. Structure layer 62 is formed of a pliable material, such as one or more of the above-described structure layer materials. Structure layer 62 comprises a single, generally rectangular panel which wraps around the arm, with longitudinal edges that meet or overlap along a line extending generally along the length of the arm. Structure layer 62 can also be formed from plural panels. Intervening elastomeric layer 63, gel layer 64 and thermal treatment layer 28 are detached or detachable from structure layer 62 at least in the vicinity of the longitudinal edges of structure layer 62. The thermal treatment layer is typically disposed between the gel and intervening layers and is coupled to and controlled by controller 23 to thermally treat the sleeve to a desired temperature in accordance with temperature sensor measurements in substantially the same manner described above.

Specifically, a first longitudinal edge portion 58 of structure layer 62 is detached from edge portion 66 of underlying intervening layer 63 and a second longitudinal edge portion 67 of structure layer 62 is detached from edge portion 65 of underlying intervening layer 63. Structure layer edge portions 58 and 67 overlap with intervening layer edges 65 and 66 in an interleaved manner, much like the edges portions of the vest garment shown in FIG. 3. Specifically, the second intervening layer edge portion 65 extends over first intervening layer edge portion 66 but beneath first structure layer edge portion 58 (i.e., between edge portions 66 and 58), and the first structure layer edge portion 58 extends over the second intervening layer edge portion 65 and beneath the second structure layer edge portion 67 (i.e., between edge portions 65 and 67).

Fasteners 68 and 69 are attached to the longitudinal edges of structure layer 62 to enable the longitudinal edges to be secured to each other in an overlapped manner. By way of non-limiting example, fasteners 68 and 69 can be complementary hook and loop fasteners. To account for variation in the degree of overlap, the fasteners of at least one of the sets of fasteners 68 and 69 have a rectangular shape, extending longitudinally in the horizontal direction to permit engagement of the fasteners over a range of overlap positions.

Sleeve 60 shown in FIG. 4 is an example of a garment of the present invention having a structure layer with edge portions detachably secured to each other with fasteners, but with no edges permanently secured to each other along seams. Other embodiments of the present invention may include a structure layer with only permanently secured edges and no detachably securable edges. For example, a glove or mitten (not shown) to be fitted over the hand can include an inner gel layer lining, an intermediate thermal treatment layer and an outer structure layer formed of two or more panels sewn together, with a single opening for the wrist/arm (with no edges detachably securable with fasteners).

Figure 5:
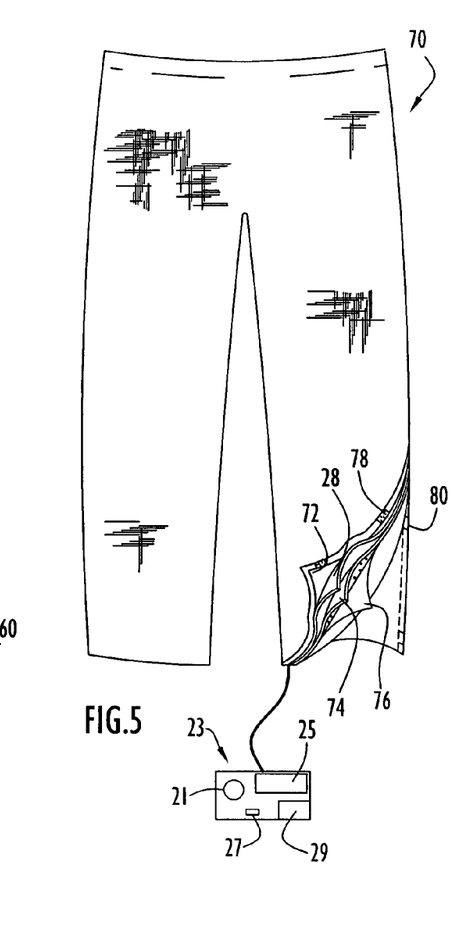
FIG. 5 is a front view in elevation of a thermal treatment garment for the lower body in accordance with another embodiment of the present invention.

Referring to FIG. 5, according to yet another embodiment of the present invention, a thermal treatment garment 70 in the form of leggings for covering skin or wounds below the waist and on the legs is shown. Leggings 70 include an outer structure layer 72 formed of a pliable material, an inner lining gel layer 74 formed of a self-adhesive, sheet-like gel material and thermal treatment layer 28 disposed between the gel and structure layers. The structure, thermal treatment and gel layers and arrangement are similar to those described above. Gel layer 74 is covered with a protective thin, peelable layer 76, such as a plastic film, to prevent gel layer 74 from accidentally contacting other surfaces prior to application to the wound. The thermal treatment layer is coupled to and controlled by controller 23 to thermally treat garment 70 to a desired temperature in accordance with temperature sensor measurements in substantially the same manner described above.

Structure layer 74 is formed of a number of panels that are seamed together in much the same way as conventional pants or trousers. However, to avoid the need to slide the leggings over the legs and hips, the leggings are preferably detachably securable along the outseam of each leg portion of leggings 70. For example, as shown in FIG. 5, the front left leg panel (e.g., the left leg panel with respect to a wearer as viewed in FIG. 5) is detachably securable to the back left leg panel along the left outseam with fasteners, such as complementary hook and loop fasteners 78 and 80 respectively attached to the corresponding edges of the front and back left leg panels. Although not explicitly shown in FIG. 5, the front and back right leg panels of leggings 70 (e.g., the right leg panel with respect to a wearer as viewed in FIG. 5) can also be detachably securable along the right outseam. If only a selected portion of the lower body is to be covered, unnecessary portions of the leggings can be removed or cut off from the portion applied to the skin or wound. For example, if only the left leg requires to be covered, gel layer 74 and/or thermal treatment layer 28 can be removed from leggings over all but the left leg portion of the leggings (leaving intact the structure layer), or the left leg portion of the leggings (the structure, gel and thermal treatment layers) can be completely detached from the rest of the leggings.

It will be appreciated that the embodiments described above and illustrated in the drawings represent only a few of the many ways of implementing a thermal treatment garment and method of thermally treating body portions.

The garments described above may be applied to any portions of a human or animal body for any type of wound, bruise, sensitive area or for promotion of healing (e.g., burns, scars, skin disorders, muscle pulls, muscle strains, sprains, swelling or inflammation, circulatory problems, blood clots, etc.). The garments may be of any size or shape to accommodate any portions of bodies or any sized users. The garments can be formed to cover any portion of the body, including any one, combination, or portion of the following body parts: fingers, hands, wrists, elbows, shoulders, arms, the head, the scalp, the face and individual facial features, the neck, the torso, the back, the breasts, the waist, hips, the groin or genitals, legs, knees, ankles, feet, and toes. Thus, the garment of the present invention can be any one, portion or combination of the following garments or articles: a finger wrap, a glove, a mitt, head or wrist bands, a sleeve, a vest, a jacket or coat, shirt, sweater, a mask, a skull cap, a neck tube, a girdle, shorts, pants, leggings, a leg wrap, a sock, a toe wrap, scarf, undergarment, blanket (e.g., baby blanket, cover or quilt, etc.), bed sheet, etc. The vest may further include openings or garments for other body portions (e.g., sleeves, a neck portion, leg portions, etc.). The garments may include any quantity of panels of any shape or size fastened together at any suitable locations by any conventional or other fastening techniques or mechanisms (e.g., sewing, stitching, staples, heat fusing where the panels of the structure layer comprise an elastomeric or thermoplastic material, etc.). The garments may be of the pullover type, or be detachable at any locations to permit placement over body portions. The garments may include any quantity of any type of conventional or other fasteners (e.g., hook and loop fasteners, buckles, buttons, clasp or clipping mechanisms, snaps, straps with locking rings, zippers, string or fabric ties, straps or frictional force, etc.) disposed at any locations to secure the garment about a body portion. The edges of the garments and/or the garment layers (e.g., thermal treatment, structure, gel and/or intervening layers) may overlap or interleave in any fashion (e.g., individually or in any combination) and may be secured in any manner to facilitate placement of the garment over a body portion. In addition, the garments may be adjustable and, by way of example, include fasteners or straps that enable adjustment of the garment to accommodate various sized users or body portions.

The structure layer of the garments may include any quantity of layers of any suitable materials (e.g., nylon mesh, woven fabrics and textiles formed of natural and/or synthetic materials, non-woven fabrics and textiles formed of natural and/or synthetic materials, elastomeric materials, etc.). The intervening layer of the garments may include any quantity of layers of any suitable materials (e.g., a galvanized or ungalvanized elastomeric material or other material to which the gel layer may adhere, etc.). The protective layer of the garments may similarly include any quantity of layers of any suitable materials (e.g., plastic film, etc.). The structure, gel, thermal treatment, intervening and protective layers of the garments may be of any quantity, shape or size having any desired thickness and may be arranged in any desired fashion.

The gel layer of the garments may be disposed on any portions or quantity of portions of the structure, thermal and/or intervening layers. The gel layer may be disposed on the garments via any conventional or other fastening techniques (e.g., by the inherent self-adhesiveness of the gel material, pressure (e.g., pressing the layers together), heat, suitable adhesive, etc.). The gel layer can be bonded to the panels of the structure or other layers prior to securing the panels together, or the panels of the structure layer can be secured together prior to lining the garments with the gel and other layers. The gel layer of the garments may be secured to and detachable from any portion or portions of the structure, thermal treatment and intervening layers. The gel layer may include any quantity of segments of any shape or size disposed at any suitable locations within the garments. The gel layer may include any quantity of any additives (e.g., anti-microbial or other agents, medicaments, ointments, lotions, Aloe, Vitamin E or other vitamins, etc.), and may be implemented by a silicone gel, hydrogel, polyurethane gel or other suitable materials. The gel layer may have any degree of self-adhesiveness (e.g., including no or minimal self-adhesive properties). The gel layer preferably directly contacts the skin of a wearer, but may indirectly contact the wearer skin to thermally treat body portions (e.g., may contact wearer clothes or other articles, etc.). In addition, the gel layer may maintain a body portion relatively stationary with respect to the garment to prevent injury due to the body portion rubbing against the garment. For example, the gel layer of a garment in the form of a bra may maintain breast nipples (and/or the corresponding breasts) of a user (e.g., girl, woman, etc.) substantially stationary to prevent injury from rubbing (e.g., during walking, running, jogging, aerobics or any other activities).

The thermal treatment layer may be of any quantity and may be disposed at any suitable locations on or within the garments (e.g., on any portions or quantity of portions of the structure, gel and/or intervening layers). The thermal treatment layer may be disposed on the garments and/or to any of the other layers (e.g., structure, gel and/or intervening layer) via any conventional or other fastening techniques (e.g., by the inherent self-adhesiveness of the gel material, pressure (e.g., pressing the layers together), heat, suitable adhesive, etc.). The thermal treatment layer of the garments may be secured to and detachable from any portion or portions of the structure, gel and intervening layers.

The thermal treatment layer may include any type of thermal element to heat and/or cool the garment (e.g., heating pad, coils, wires, thermoelectric device, radiation, etc.). The thermal treatment layer may heat and/or cool the garment in any combination or fashion (e.g., heat, cool or heat and cool the garment). The thermal treatment layer may include any structure or housing to include the thermal element or the thermal element or layer may be embedded within other garment layers in any fashion.

The thermal treatment layer may include any quantity of segments or units of any shape or size disposed at any suitable locations within the garments (e.g., FIG. 3). The units may individually thermally treat the gel layer or wearer and each may be controlled by a corresponding or common controller (e.g., and temperature sensor) to the same or different temperature. The units may be detachable from the garment to enable thermal treatment of particular garment portions.

The controller may be implemented by any quantity of any conventional or other microprocessor, controller and/or circuitry and may control any quantity of thermal treatment layers or elements. The controller may control plural thermal treatment layers to the same or different temperatures, or a plurality of thermal treatment layers may each be controlled by a corresponding controller to the same or different temperatures. The controller may control the thermal treatment layer to any desired temperature or temperature range. By way of example only, the thermal treatment layer may be controlled to any temperature or range within twenty to one-hundred ten degrees Fahrenheit. The display may be implemented by any conventional or other display and display any desired information (e.g., set point temperature, actual temperature, time, date, etc.) in any scales or units. The power switch may be of any quantity, may be disposed at any location and may be implemented by any conventional or other switch (e.g., momentary, button, etc.). The input devices may be of any quantity, may be disposed at any locations and may be implemented by any conventional or other input devices (e.g., buttons, switches, keys, touch screen, etc.). The input devices may facilitate entry of any desired information (e.g., set point temperature, etc.). The controller may further maintain and display an elapsed time of thermal treatment when a garment is to be utilized for a prescribed time interval. The controller or garment may include an alarm (e.g., audio, visual, etc.) to indicate when a desired temperature or range is attained (or exceeded) or when a time interval expires.

The temperature sensor may be of any quantity, may be disposed at any locations on or within the garment and may be implemented by any conventional or other temperature sensing device (e.g., RTD, infrared, etc.). The controller may control the thermal treatment layer in accordance with a preset or predetermined temperature or a user entered temperature or temperature range. The controller may utilize any quantity of user specified temperatures (e.g., maximum temperatures, minimum temperatures, etc.). Alternatively, the controller or other control device may be in the form of a power source to provide a safe power signal to the thermal treatment layer (e.g., without monitoring temperature or receiving temperature range information). The temperature sensor and thermal treatment layer may be coupled to the controller via any conventional or other communication medium (e.g., wire or cable, wireless transmission, etc.). The controller power source may be implemented by any type of conventional or other power source (e.g., batteries to enable transport, AC, DC, from a wall, vehicle or other outlet jack, etc.).

It is to be understood that the terms "left", "right", "front", "back", "rear", "top", "bottom", "upper", "lower", "horizontal", "vertical", "height", "length", "width", "thickness" and the like are used herein merely to describe points of reference and do not limit the present invention to any particular configuration or orientation.

From the foregoing description, it will be appreciated that the invention makes available a novel thermal treatment garment and method of thermally treating body portions, wherein a garment includes a thermal element to thermally treat garment gel material directly contacting the skin of a wearer.

Having described preferred embodiments of a new and improved thermal treatment garment and method of thermally treating body portions, it is believed that other modifications, variations and changes will be suggested to those skilled in the art in view of the teachings set forth herein. It is therefore to be understood that all such variations, modifications and changes are believed to fall within the scope of the present invention as defined by the appended claims.

What is claimed is:

1. A thermal treatment article for thermally treating body portions comprising:
   a structure layer formed of a pliable material, said structure layer having an inner surface that faces generally toward a user;
   a self-adhesive gel layer removably adhered to the inner surface of said structure layer and forming an interior surface of the article, wherein said gel layer directly contacts skin of said user;
   a thermal treatment layer coupled to said gel layer to thermally treat said gel layer and said user;
   a temperature sensor to measure temperature of a portion of at least one of said article and said user; and
   a controller to control said thermal treatment layer to thermally treat said gel layer and said user, wherein said controller includes an input device to facilitate entry of a desired temperature and controls said thermal treatment layer in accordance with said measured temperature to attain said desired temperature.

2. The article of claim 1, wherein said article is one of a wound dressing garment, a finger wrap, a headband, a wristband, a sleeve, a vest, a jacket, a coat, a shirt, a sweater, a neck tube, a girdle, shorts, pants, leggings, a leg wrap, a toe wrap, and an undergarment.

3. The article of claim 1, wherein the article is suitable for enveloping at least a portion of at least one of: a finger, a hand, a wrist, an elbow, a shoulder, an arm, a head, a scalp, a face, a neck, a torso, a back, at least one breast, a waist, a groin, at least one genital, a hip, a leg, a knee, an ankle, a foot and a toe.

4. The article of claim 1, wherein said controller includes a display to display at least one of said desired temperature and said measured temperature.

5. The article of claim 1, wherein said thermal treatment layer includes a thermal element to thermally treat said gel layer and said user.

6. The article of claim 5, wherein said thermal element includes a heater to heat said gel layer and said user.

7. The article of claim 5, wherein said thermal element includes a cooling unit to cool said gel layer and said user.

8. The article of claim 5, wherein said thermal element heats and cools said gel layer and said user.

9. The article of claim 1, wherein said gel layer is separable from said article and said thermal treatment layer includes a plurality of thermal units each thermally treating a portion of said gel layer and said user, and wherein each said thermal unit is detachable from said article to enable thermal treatment of selected portions of said user.

10. The article of claim 1, wherein said gel layer comprises one of a hydrogel gel and a polyurethane gel.

11. The article of claim 1, wherein said gel layer directly contacts a wound on said user skin.

12. The article of claim 1, wherein said gel layer includes a medicament for application to said user skin.

13. The article of claim 1, wherein said article is adjustable to accommodate users of varying sizes.

14. A method of thermally treating body portions via an article including a structure layer formed of a pliable material with an inner surface that faces generally toward a user, a temperature sensor, a controller including an input device to facilitate entry of a desired temperature and a gel layer coupled to the inner surface of said structure layer and forming an interior surface of the article, said method comprising:
   (a) receiving a body portion within said article, wherein said gel layer is self-adhesive and removably adhered to said structure layer inner surface and directly contacts skin of said user;
   (b) applying thermal energy to said gel layer and said body portion; and
   (c) measuring temperature of a portion of at least one of said article and said user and controlling said application of said thermal energy to thermally treat said gel layer and said body portion received in said article in accordance with said measured temperature to attain said desired temperature.

15. The method of claim 14, wherein said article is one of a wound dressing garment, a finger wrap, a headband, a wristband, a sleeve, a vest, a jacket, a coat, a shirt, a sweater, a neck tube, a girdle, shorts, pants, leggings, a leg wrap, a toe wrap, and an undergarment.

16. The method of claim 14, wherein said body portion is at least a portion of at least one of: a finger, a hand, a wrist, an elbow, a shoulder, an arm, a head, a scalp, a face, a neck, a torso, a back, at least one breast, a waist, a groin, at least one genital, a hip, a leg, a knee, an ankle, a foot and a toe.

17. The method of claim 14, wherein step (c) further includes:
   (c.1) displaying at least one of said desired temperature and said measured temperature.

18. The method of claim 14, wherein step (b) further includes:
   (b.1) applying said thermal energy to heat said gel layer and said body portion.

19. The method of claim 14, wherein step (b) further includes:
   (b.1) applying said thermal energy to cool said gel layer and said body portion.

20. The method of claim 14, wherein step (b) further includes:
   (b.1) applying said thermal energy to selectively heat and cool said gel layer and said body portion.

21. The method of claim 14, wherein step (b) further includes:
   (b.1) applying thermal energy to only selected sections of said body portion received in said article.

22. The method of claim 14, wherein step (a) further includes:
   (a.1) receiving said body portion within said article with said gel layer directly contacting a wound on said body portion skin.

23. The method of claim 14, wherein said gel layer includes a medicament and step (a) further includes:
   (a.1) applying said medicament to said body portion skin.

24. The method claim of claim 14, wherein said article is adjustable and step (a) further includes:
   (a.1) adjusting dimensions of said article to accommodate users of varying sizes.

\* \* \* \* \*